(12) United States Patent
Golz-Berner et al.

(10) Patent No.: US 7,968,129 B2
(45) Date of Patent: Jun. 28, 2011

(54) COSMETIC SKIN CARE COMPLEX WITH ANTI-AGING EFFECT

(75) Inventors: Karin Golz-Berner, Monaco (MC); Leonhard Zastrow, Monaco (MC)

(73) Assignee: Coty Prestige Lancaster Group GmbH, Mainz (DE)

( * ) Notice: Subject to any disclaimer, the term of this patent is extended or adjusted under 35 U.S.C. 154(b) by 169 days.

(21) Appl. No.: 12/307,180

(22) PCT Filed: Jun. 28, 2007

(86) PCT No.: PCT/EP2007/056494
§ 371 (c)(1),
(2), (4) Date: Jan. 15, 2009

(87) PCT Pub. No.: WO2008/003638
PCT Pub. Date: Jan. 10, 2008

(65) Prior Publication Data
US 2009/0196895 A1 Aug. 6, 2009

(30) Foreign Application Priority Data
Jul. 5, 2006 (DE) .......................... 10 2006 031 762

(51) Int. Cl.
*A61K 36/00* (2006.01)
*A61K 31/685* (2006.01)
*A61K 8/02* (2006.01)
*A61K 51/00* (2006.01)
*A61K 36/899* (2006.01)

(52) U.S. Cl. ........ 424/725; 424/401; 424/774; 424/776; 424/1.21; 424/750

(58) Field of Classification Search .................. None
See application file for complete search history.

(56) References Cited

U.S. PATENT DOCUMENTS
2005/0079210 A1* 4/2005 Gupta .......................... 424/450

FOREIGN PATENT DOCUMENTS

| EP | 0826366 | | 3/1998 |
| FR | 2578422 A | * | 9/1986 |
| JP | 01083007 A | * | 3/1989 |
| RU | 2146123 C1 | * | 3/2000 |
| WO | WO 03/013562 | | 2/2003 |
| WO | WO 2006/048158 | | 5/2006 |

OTHER PUBLICATIONS

Bondioli et al, Alpha linolenic acid rich oils. Composition of Plukenetia volubilis (Sacha Inchi) oil from Peru, Rivista italiana delle Sostanze Grasse, (2006) 83 (3): 120-123.*

Schilcher, Chromatographic analyses of drugs, drug preparations and active substances in pharmacognosy, balneology and cosmetology, Cynarin determination in artichoke leaves and artichoke preparations, Sciential Pharmaceutica 1971; 39 (3): 151-158.*

* cited by examiner

*Primary Examiner* — Qiuwen Mi
(74) *Attorney, Agent, or Firm* — Novak Druce + Quigg LLP

(57) ABSTRACT

The invention relates to a cosmetic preparation which includes a skin care complex having an anti-ageing effect. The complex consists of liposomes comprising a mixture of cosmetic oil, extract of *Plukenetia volubilis* seeds, extract of *Cynara scolymus* leaves and hydrogenated retinol. The liposomes are homogeneously dispersed in a gel network consisting of water and a gel-forming agent.

5 Claims, No Drawings

COSMETIC SKIN CARE COMPLEX WITH ANTI-AGING EFFECT

CROSS-REFERENCE TO RELATED APPLICATIONS

This application is a §371 national stage of PCT/EP2007/056494, filed Jun. 28, 2007, the entirety of which is hereby incorporated by reference.

BACKGROUND OF THE INVENTION

The invention relates to a cosmetic preparation which includes a skin care complex having an anti-ageing effect.

A large number of cosmetic products with anti-ageing effect are already known. Essential components of many well-known products are retinol or derivatives thereof, i.e. retinoic acid, retinyl palmitate, tocopherol retinoate, $C_2$-$C_5$ esters of retinol, and others. However, the effect of these products is not always satisfactory because the stability is frequently insufficient so that the effectiveness is rapidly reduced and, in addition, skin irritations may arise.

EP 826 366 describes the reduction of irritative effects of hydroxy acids or retinol/retinoids by addition of borage seed oil in aqueous systems.

DETAILED DESCRIPTION OF THE INVENTION

The invention is based on the object of providing a skin care cosmetic product with anti-ageing effect, which shows rapid effectiveness, maintains the effect for a long period of time, and has no skin-irritating side effects.

According to the invention, a cosmetic preparation including a skin care complex with anti-ageing effect is provided, wherein said complex consists of liposomes comprising a mixture of cosmetic oil, extract of *Plukenetia volubilis* seeds, extract of *Cynara scolymus* leaves and hydrogenated retinol, said liposomes are homogeneously dispersed in a gel network of water and a gel-forming agent, and said complex in the form of the gel, together with common cosmetic additives, adjuvants, active substances and mixtures thereof, is included in the cosmetic preparation at a concentration of 0.1-11 wt. %. The concentration data are based on the overall weight of the preparation.

Concentrations of the gel, i.e. of the complex, in the preparation in the range of from 1 to 6 wt. % are particularly preferred.

It was found that the combination of Inca inchi (*Plukenetia volubilis*) seed extract, artichoke (*Cynara scolymus*) leaves extract and hydrogenated retinol not only has particularly rapid effectiveness but also maintains the anti-ageing effect over a long period of time. For rapid and high initial effectiveness, it is essential that the liposomes be embedded in a gel network, wherein it is only upon contact with the skin that the liposomes, isolated from each other, are destroyed due to different electric charges of skin/liposome and release the active substances which immediately develop their full effectiveness.

The mechanism involved in such long-lasting effectiveness still remains unresolved but is presumably based on a synergistic effect of the two plant extracts with hydrogenated retinol. The effectiveness is particularly significant in mature skin of users more than 50 years of age. As illustrated in the examples, it is particularly in this type of skin that the number and depth of wrinkles is significantly reduced.

More specifically, the liposomes formed with water and the oils being employed are phospholipid liposomes well-known from the prior art. They are completely closed lipid bilayer membranes containing an entrapped aqueous volume. Liposomes may be unilamellar vesicles (having a single-membrane bilayer) or multilamellar vesicles (onion-like structures characterized by multiple membrane bilayers, each separated from the next by an aqueous layer). The bilayer is constituted of two lipid monolayers having a hydrophobic "tail" region and a hydrophilic "head" region. The structure of the membrane bilayer is such that the hydrophobic (non-polar) "tails" of the lipid monolayers orient toward the center of the bilayer, while the hydrophilic "heads" orient towards the aqueous phase.

The production of liposomes from saturated and unsaturated lipids as well as the use thereof as transport system has been described in a large number of patents. Incorporation of the skin care complex of the invention can be effected in the usual manner.

For example, phosphatidyl choline, phosphatidyl ethanolamine, phosphatidyl inositol, phosphatidyl serine, phosphatidic acid and lysolecithins as well as mixtures thereof can be employed as phospholipids. Well-known products are Phoslipon® or NATO, for example.

The gel receiving the liposomes is preferably one that consists of an acrylate polymer, e.g. Pemulen TR1® Polymeric Emulsion (INCI: Acrylates/$C_{10\text{-}30}$ Alkyl Acrylate Crosspolymer), which, in the present case, acts as gel-forming agent, i.e., forms a highly active aqueous microgel with water, which keeps the oil droplets isolated from each other. At the same time, the hydrophobic portions of the polymer are anchored in the oil phase.

The Inca inchi (*Plukenetia volubilis*) seed extract used in the skin care complex is a product produced by cold pressing of the seeds and subsequent purification by decantation and filtration.

The share of Inca inchi extract is 1.0 to 3 wt. %, relative to the composition of the complex.

The artichoke (*Cynara scolymus*) leaves extract used in the skin care complex is an extract obtained at room temperature (15-25° C.) with propylene glycol. Up to now, artichoke leaves have largely been used in foodstuffs and occasionally, together with other vegetable products, in cosmetic hair products.

The use of artichoke plants described in WO 99/61035 relates to an orally administered pharmaceutical preparation for the treatment of hyperlipidemia.

The share of artichoke leaf extract is from 2 to 4 wt. %, relative to the composition of the complex.

The hydrogenated retinol that is used is a retinol wherein all double bonds have been saturated by hydrogenation. This product shows improved light and heat stability and less skin irritation compared to native retinol. It is preferably present in a 10% preparation with caprylic/capric acid triglyceride and is used in this form.

The share of hydrogenated retinol in the preferred preparation is from 0.1 to 1 wt. %, relative to the composition of the complex.

In general, the complex consists of water, 3 to 10 wt. % phospholipids, 0.3 to 1 wt. % gel-forming agent, 3 to 10 wt. % monohydric alcohol (e.g. ethanol), 5 to 12 wt. % polyhydric alcohol (e.g. glycerol), the active principles Inca inchi extract with 1 to 3 wt. %, artichoke extract with 2 to 4 wt. %, hydrogenated retinol with 0.1 to 1 wt. %, and further adjuvants such as preservatives, TEA, oils etc.

In the form of a preparation, the skin care cosmetic agent may also include well-known adjuvants and vehicles such as commonly used in such preparations, e.g. water, preservatives, dyes, pigments having a coloring effect, thickening agents, odorous substances, alcohols, polyols, oils, esters, electrolytes, gel-forming agents, copolymers, silicone emulsifiers, waxes, stabilizers, and mixtures thereof.

The oils used in the invention can be conventional cosmetic oils, such as mineral oil; hydrogenated polyisobutene, squalane produced synthetically or from natural products; cosmetic esters or ethers which can be branched or unbranched, saturated or unsaturated; vegetable oils, or mixtures of two or more thereof.

Especially suitable oils are vegetable oils having high contents of omega-3 and omega-6 fatty acids, e.g. nut oils such as hazelnut oil. It is also possible to use other vegetable oils such as calendula oil, jojoba oil, avocado oil, macadamia nut oil, castor oil, cocoa butter, coconut oil, maize oil, cottonseed oil, olive oil, palm nut oil, rape seed oil, safflower oil, sesame oil, soybean oil, sunflower oil, wheat germ oil, grape seed oil, candlenut oil, thistle oil and mixtures thereof. However, the contribution of these other oils in achieving the desired direction of effects is limited.

The cosmetic product may also contain further active substances, including inorganic and organic light stabilizers, self-tanning agents, free-radical scavengers, vitamins, enzymes, further plant active substances, polymers, antioxidants and omega-3/6 fatty acids.

Antioxidants include vitamins such as vitamin C and derivatives thereof, e.g. ascorbyl acetate, phosphate and palmitate, magnesium ascorbyl phosphate; vitamin A and derivatives thereof; folic acid and derivatives thereof, vitamin E and derivatives thereof, such as tocopheryl acetate; flavones or flavonoids; amino acids such as histidine, glycine, tyrosine, tryptophan and derivatives thereof; imidazoles such as cis- or trans-urocaninic acid and derivatives thereof; peptides such as D,L-carnosine, D-carnosine, L-carnosine and derivatives thereof; carotenoids and carotenes such as α-carotene and β-carotene, lycopene; uric acid and derivatives thereof; α-hydroxy acids such as citric acid, lactic acid, malic acid; α-hydroxyfatty acids such as palmitic acid, phytic acid, lactoferrin; stilbenes and derivatives thereof; mannose and derivatives thereof; lipoic acid and derivatives thereof, e.g. dihydrolipoic acid; ferulic acid and derivatives thereof; thiols such as glutathione, cysteine, cystine and esters thereof; folic acid and derivatives thereof.

Preferred antioxidants or free-radical scavengers are plant extracts, particularly those selected from the group consisting of *Angelica archangelica, Arnica montana, Camellia sinensis, Cupressus semper, Coffee arabica, Polygonatum multiflorum, Pongamia pinnata, Rosmarinus officinalis, Evernia fufuracea, Evernia prunastri, Aventa sativa* and mixtures thereof.

Specifically preferred as free-radical scavengers are vitamin A, vitamin E, peptides, flavones, flavonols, as well as plant extracts. An especially advantageous plant extract is one made of dried extracts of *Angelica archangelica, Camellia sinensis, Coffee arabica* and *Pongamia pinnata* in a monohydric alcohol.

The cosmetic product according to the invention can also be added with appropriate water- and/or oil-soluble UVA or UVB filters, or both, but preferably only to such an extent that a sun protection factor, SPF, of 8 is reached (determination in accordance with Colipa standard (Colipa Ref.: 94/289 (1994)). Advantageous oil-soluble UVB filters include 4-aminobenzoic acid derivatives such as 2-ethylhexyl 4-dimethylaminobenzoate; esters of cinnamic acid such as 2-ethylhexyl 4-methoxycinnamate; benzophenone derivatives such as 2-hydroxy-4-methoxybenzophenone; 3-benzylidenecamphor derivatives such as 3-benzylidenecamphor.

Preferred oil-soluble UV filters are benzophenone-3, butyl-methoxybenzoylmethane, octyl methoxycinnamate, octyl salicylate, 4-methylbenzylidenecamphor, homosalates and octyl dimethyl PABA.

Water-soluble UVB filters are, for instance, sulfonic acid derivatives of benzophenone or of 3-benzylidenecamphor or salts such as the Na or K salt of 3-phenylbenzimidazole-5-sulfonic acid.

The UVA filters include dibenzoylmethane derivatives such as 1-phenyl-4-(4'-isopropylphenyl)propane-1,3-dione, butyl-methoxybenzoylmethane and menthyl anthranilate.

Particularly preferred are benzophenone-3, butylmethoxydibenzoylmethane, octyl methoxycinnamate, octyl salicylate, 4-methylbenzylidenecamphor, homosalates, octocrylene, ethylhexyl methoxycinnamate, isoamyl p-methoxycinnamate, octyl dimethyl PABA, ethylhexyltriazone, diethylhexylbutamidotriazone, ethylhexyl salicylate, methylene-bis(benzotriazolyl)tetramethylbutylphenol, disodium phenyldibenzimidazole tetrasulfonate, bis-ethylhexyloxyphenol methoxy-phenyltriazine.

Furthermore, broad-spectrum filters such as bis-resorcinyltriazine derivatives or benzoxazoles can be employed.

For example, the pigments, pigment mixtures or powders having a pigment-like effect, also including those having a nacreous effect, which are added to the cosmetic product may comprise iron oxides, natural aluminum silicates such as ocher, titanium dioxide, mica, kaolin, manganese-containing clays, calcium carbonate, talc, mica-titanium oxide, mica-titanium oxide-iron oxide, nylon beads, ceramic beads, expanded and non-expanded synthetic polymer powders, powdered natural organic compounds such as ground solid algae, ground plant parts, encapsulated and non-encapsulated grain starches.

Further materials suitable as active substances are self-tanning agents such as isatin, alloxan, ninhydrin, glyceraldehyde, meso-tartaraldehyde, glutaraldehyde, erythrulose, pyrazoline-4,5-dione derivatives, dihydroxyacetone (DHA), 4,4-dihydroxypyrazoline-5-dione derivatives.

Another additive for the cosmetic product of the invention is an active substance preparation according to WO99/66881 with a high free-radical protection factor and with a content of a product obtained by extraction of the bark of Quebracho blanco and subsequent enzymatic hydrolysis, which product includes at least 90 wt. % of proanthocyanidin oligomers and at most 10 wt. % of gallic acid, in microcapsules, and a silkworm extract obtained by extraction, which includes the peptide cecropin, amino acids and a vitamin mixture, and a non-ionic, cationic or anionic hydrogel or a mixture of hydrogels, and one or more phospholipids, and water.

As additional active substance, a preparation with plant extracts according to WO 2004/105704 is also particularly preferred, which includes alcohol-based plant extracts consisting of 0.1 to 2 wt. % of an extract of green coffee beans, 0.1 to 2 wt. % of an extract of *Camellia sinensis* leaves, 0.1 to 2 wt. % of an extract of Pongamia pinnata and 0.1 to 2 wt. % of an extract of *Angelica archangelica* roots and a balance of a monohydric $C_2$-$C_5$ alcohol to make 100 wt. %, the free-radical protection factor ranging from 1,400 to 2,900×$10^{14}$ radicals per mg.

Also, omega-3 fatty acids, omega-6 fatty acids or mixtures thereof are preferred as additional active substances. Omega-3 fatty acids include α-linolenic acid, eicosapentaenoic acid and docosahexaenoic acid. Omega-6 fatty acids include linolic acid, arachidonic acid and γ-linolenic acid. These fatty acids are so-called essential fatty acids in the nutrition of humans and, together with the active substances of the present invention, are also capable of further improving the anti-ageing effect on the skin. Contents of 1 to 6 wt. % are preferred, especially 2 to 4.5 wt. %.

The invention also relates to a method of producing the specific skin care complex, i.e., the preparation. According to the invention, a) one or more oils and the active ingredients Inca inchi extract, artichoke extract and hydrogenated retinol are mixed with alcohol and water at 15-25° C. to form a first mixture; subsequently,
b) the first mixture produced under a) is added to a separately produced second mixture at an addition rate of no more than 10 g/min at 1,000-3,000 rpm, said second mixture consisting of a phospholipid and optionally further adjuvants and active substances;
c) the third mixture thus formed is stirred at 600-800 rpm until the liposomes are formed;
d) water and the gel-forming agent are combined and stirred at no more than 1,200 rpm until a gel network is formed; and
e) the third mixture is introduced into the gel of step d) at less than 700 rpm over a period of 15-40 min;
f) the gel obtained according to e) is mixed with cosmetic adjuvants, active substances or mixtures thereof at 25 to 35° C. and less than 700 rpm.

The preparation of the invention may have any common cosmetic form, e.g. day cream, night cream, sun gel, masks, body lotions, cleansing milk, make-up, cream cleansers, lip sticks, body powders, eye beauty care, hair masks, hair rinses, hair shampoos, shower gels, shower oil, bath oil, deo sticks, perfume sticks, cooling deo rollers, deo rollers, compact powder or compact wax, optionally including applicator, rouge, grounding, sun protection preparation (sun care or after-sun).

With reference to the examples, the invention will be illustrated in more detail below. All data are given in percent by weight, unless otherwise stated.

EXAMPLE 1

Production of the 50+ Skin Care Complex

|  | % |
| --- | --- |
| Phase A | |
| Lecithins | 5-8 |
| Glycerol | 8-10 |
| Wheat germ oil | 1-3 |
| Phase B | |
| Water | 40 |
| Alcohol | 5-7 |
| Hazelnut oil | 2-5 |
| Inca inchi seed extract | 1-3 |
| Artichoke leaves extract (in PPG) | 2-4 |
| Retinol, hydrogenated | 0.1-1 |
| Preservative | 0.5-1 |
| Phase D | |
| Water | q.s. ad 100 |
| Acrylates/$C_{10-30}$ alkyl acrylate crosspolymer | 0.3-0.5 |
| Triethanolamine | 0.3-0.5 |
| Preservative | 0.5 |

Following addition of all components, phase A is homogenized with at least 2,000 rpm for about 40-60 minutes at 20-40° C. Separately, the components of phase B are combined at 500-600 rpm and stirred for 20 minutes. Phase B is added very slowly to phase A (about 1 hour for a total of 1 kg of mixture) with stirring at about 3,000 rpm and at temperatures below 40° C., and the two phases form the liposomes of phase C, which are stirred at about 600-800 rpm.

Separately, the gel-forming agent of phase D is placed in water and stirred at about 1,000 rpm for 10 minutes until formation of the gel network is obtained. Thereafter, phase C is added to phase D at about 600 rpm for 30 minutes to obtain about 1 kg of product (the 50+ complex).

EXAMPLE 2

Day Cream Cosmetic Preparation

| Phase A | |
| --- | --- |
| Water | q.s. ad 100 |
| Disodium EDTA | 0.1 |
| Propylene glycol | 2 |
| Glycerol | 5 |
| Phase B | |
| Chlorphenesin | 0.5 |
| Diisopropyl sebacate | 9 |
| Cetearyl alcohol (75° C.) | 2 |
| Cyclohexasiloxane & cyclopentasiloxane | 3 |
| Phase C | |
| Phase C is formed from phases A and B combined at 75° C., homogenized for 5 minutes and cooled down to 35° C. at about 3,000 rpm. | |
| Phase D | |
| Homogenizing agent | 0.3 |
| Perfume | 0.5 |
| Complex 50+ of Example 1 | 10 |
| (Inca inchi 1.5%, artichoke 2.5%, retinol hydr. 0.4%, relative to the overall weight of the complex) | |
| Phase D is mixed with phase C at 20-35° C. and less than 1,000 rpm. | |

EXAMPLE 3

Eye Cream Cosmetic Preparation

| Phase A | |
| --- | --- |
| Water | q.s. ad 100 |
| EDTA | 0.3 |
| Glycerol | 5 |
| Phase B | |
| PEG 100 stearate glyceryl stearate | 4 |
| Shea butter | 2 |
| Cetearyl alcohol (70° C.) | 3.5 |
| Cyclopentasiloxane & dimethiconol | 5 |
| Phase C | |
| Phase C is formed from phases A and B combined at 75° C., homogenized for 5 minutes and cooled down to 35° C. at about 3,000 rpm. | |
| Phase D | |
| Perfume | 0.5 |
| RPF complex ® | 1 |
| Complex 50+ of Examples 1 and 2 | 5 |
| Preservative | 0.3 |

Production as in Example 2.

EXAMPLE 4

Cream Cleanser Cosmetic Preparation

| Phase A | |
|---|---|
| Water | q.s. ad 100 |
| EDTA | 0.1 |
| Propylene glycol | 3.5 |
| Glycerol | 3 |
| Phase B | |
| Steareth-2 | 2.5 |
| Steareth-21 | 2 |
| Glyceryl stearate | 2 |
| Dimethicone | 5 |
| Phase C | |
| Phase C is formed from phases A and B combined at 75° C., homogenized for 5 minutes and cooled down to 35° C. at about 3,000 rpm. | |
| Phase D | |
| Perfume | 0.3 |
| RPF complex ® | 0.1 |
| Complex 50+ of Examples 1 and 2 | 0.1 |
| Preservative | 0.3 |

\* According to Example 1 of WO 2004/105706.
Production as in Example 2.

EXAMPLE 5

User Test

A formulation in accordance with Example 2 was produced (A). Another formulation in accordance with Example 2 including no artichoke extract and retinol was designated (B).

Another formulation in accordance with Example 2 including usual retinol and no artichoke extract and Inca inchi was designated (C).

Another formulation in accordance with Example 2 including no Inca inchi and retinol was designated (D).

The test was performed on 15 female participants 52 to 66 years of age. The participants applied the creams A, B, C and D on four marked areas on the left and right forearm twice a day. Digitalized images of the marked sites were made at preset intervals of 2 weeks and evaluated according to number and depth of wrinkles using a computer program.

The results are shown in Table 1.

TABLE 1

| | Reduction of wrinkles [%] | | | |
|---|---|---|---|---|
| | A | B | C | D |
| Start of treatment | 0 | 0 | 0 | 0 |
| After 2 weeks | 19-21 | 5-7 | 7-11 | 4-6 |
| 4 weeks | 27-29 | 9-10 | 7-11 | 4-7 |
| 6 weeks | 33-35 | 11-12 | 10-14 | 8-9 |
| 8 weeks | 39-40 | 11-12 | 15-19 | 6-7 |
| 12 weeks | 40-42 | 10-12 | 16-18 | 7-8 |

Table 1 shows a superior effect with preparation A, thus allowing to conclude on synergism. Also, the effect is significantly improved compared to the use of retinol alone (preparation C). Moreover, the effect of preparation A according to the invention is sustained for a long period of time (12 weeks).

EXAMPLE 6

A day cream was produced in accordance with Example 2, with phase B additionally including 3% omega-3/6 fatty acids (mixture of α-linolenic acid, linolic acid and arachidonic acid). A reduction of wrinkles of 42% after 8 weeks and 43.5% after 12 weeks was found in the user test in accordance with Example 5.

The invention claimed is:

1. A cosmetic preparation, comprising:
   a skin care complex with anti-ageing effect, wherein said complex consists of liposomes comprising a mixture of cosmetic oil, extract of *Plukenetia volubilis* seeds, extract of *Cynara scolymus* leaves and hydrogenated retinol, said liposomes are homogeneously dispersed in a gel network consisting of water and a gel-forming agent, and the gel, together with common cosmetic additives, adjuvants, active substances and mixtures thereof, is included in the cosmetic preparation at a concentration of 0.1-11 wt. %, the concentration being based on the overall weight of the preparation, wherein the extract of the *Plukenetia volubilis* seeds is in the range of 1-3 wt. %, relative to the overall weight of the complex; wherein the extract of the *Cynara scolymus* leaves is in the range of 2-4 wt. %, relative to the overall weight of the complex; and wherein the concentration of hydrogenated retinol is in the range of 0.1-1 wt. %, relative to the overall weight of the complex.

2. The cosmetic preparation according to claim 1, wherein the concentration of the complex is in the range of 1-6 wt. %, relative to the overall weight of the preparation.

3. The cosmetic preparation according to claim 1, wherein omega-3/6 fatty acids are included as further active substances.

4. The cosmetic preparation according to claim 1, wherein the skin care complex consists of
   3 to 10 wt. % phospholipids,
   0.3 to 1 wt. % gel-forming agent,
   3 to 10 wt. % monohydric alcohol,
   5 to 12 wt. % polyhydric alcohol,
   1 to 3 wt. % extract of *Plukenetia volubilis* seeds,
   2 to 4 wt. % extract of *Cynara scolymus* leaves,
   0.1 to 1 wt. % hydrogenated retinol, water, and further adjuvants.

5. The cosmetic preparation according to claim 1, wherein the skin care complex consists of
   5 to 8 wt. % lecithins,
   8 to 10 wt. % glycerol,
   1 to 3 wt. % wheat germ oil,
   5 to 7 wt. % alcohol,
   2 to 5 wt. % hazelnut oil,
   1 to 3 wt. % extract of *Plukenetia volubilis* seeds,
   2 to 4 wt. % extract of *Cynara scolymus* leaves,
   0.1 to 1 wt. % hydrogenated retinol,
   1 to 1.5 wt. % preservative,
   0.3 to 0.5 wt. % acrylates/$C_{10-30}$ alkyl acrylate crosspolymer,
   0.3 to 0.5 wt. % triethanolamine, and
   q.s, ad 100 wt. % water.

\* \* \* \* \*